United States Patent [19]
Lewis

[11] Patent Number: 5,589,591
[45] Date of Patent: Dec. 31, 1996

[54] ENDOTOXIN-FREE POLYSACCHARIDES

[75] Inventor: Jerome M. Lewis, Newton, Mass.

[73] Assignee: Advanced Magnetics, Inc., Cambridge, Mass.

[21] Appl. No.: 346,142

[22] Filed: Nov. 29, 1994

Related U.S. Application Data

[63] Continuation-in-part of Ser. No. 260,551, Jun. 16, 1994, Pat. No. 5,554,386, which is a continuation-in-part of Ser. No. 936,873, Aug. 27, 1992, Pat. No. 5,336,506, which is a continuation-in-part of Ser. No. 900,686, Jun. 17, 1992, Pat. No. 5,478,576, which is a continuation of Ser. No. 630,017, Dec. 19, 1990, abandoned, which is a continuation of Ser. No. 679,526, Apr. 2, 1991, Pat. No. 5,141,739, which is a continuation of Ser. No. 384,991, Jul. 2, 1989, abandoned, which is a continuation-in-part of Ser. No. 228,640, Aug. 4, 1988, abandoned, which is a continuation-in-part of Ser. No. 67,586, Jun. 26, 1987, Pat. No. 4,827,945, which is a continuation-in-part of Ser. No. 882,044, Jul. 3, 1986, Pat. No. 4,770,183.

[51] Int. Cl.$^6$ .............................. C07H 1/00; C08B 37/00
[52] U.S. Cl. ........................... 536/128; 536/127; 536/124
[58] Field of Search ........................... 424/484; 536/128, 536/127, 124

[56] References Cited

U.S. PATENT DOCUMENTS

| | | | |
|---|---|---|---|
| 3,325,473 | 6/1967 | Herrick et al. | 260/209 |
| 3,337,526 | 8/1967 | Adams | 260/209 |
| 3,509,126 | 4/1970 | Dahl | 260/209.5 |
| 4,909,942 | 3/1990 | Sato | 210/651 |
| 4,950,751 | 8/1990 | DeWitt | 536/128 |
| 5,116,969 | 5/1992 | Adams | 536/128 |

FOREIGN PATENT DOCUMENTS

| | | |
|---|---|---|
| 1-97587 | 4/1989 | Japan . |

OTHER PUBLICATIONS

Ettling et al., Tappi 51:116–118 (1968).
Whistler ed., *Industrial Gums*, pp. 415–427, New York:Academic Press (1973).
Corash et al., J. Lab. & Clin. Med. 84:147–151.
Cooper, *The Tools of Biochemistry*, pp. 169–177, New York:John Wiley & Sons (1977).
Sharma, Biotechn. and Applied Biochem. 8:5–22 (1986).
Cheryan, *Ultrafiltration Handbook*, pp. 1–5, 53–64, Lancaster:Technomic Publishing Co. (1986).
Beutler, *Red Cell Metabolism*, pp. 99–105, Edinburgh:Churchill Livingstone (1986).
Josephson, et al., Mag. Reson. Imag. 8:637–46 (1990).
Reimer et al., Radiology 177:729–34 (1990).
Hou et al., J. Parenteral. Sci. and Tech. 44:204–209 (1990).
Hou et al., Biotech. and Applied Biochem. 12:315–324 (1990).
Millipore Corporation, Bedford, MA; promotional brochure entitled "Selecting a Membrane for Concentration, Desalting and Buffer Exchange of Macromolecules (Ultrafiltration)," Jun. 1991.
Groman et al., Bioconjugate Chemistry 5:546–556 (1994).
United States Pharmacopeia p. 1489 (1995).

*Primary Examiner*—Gollamudi S. Kishore
*Attorney, Agent, or Firm*—Bromberg & Sunstein

[57] ABSTRACT

This invention is composition comprising a highly purified, substantially endotoxin-free polysaccharide preparation suitable for use as a parenterally administered pharmaceutical, and the method for producing the composition. The process produces a substantially endotoxin-free polysaccharide composition using a size separation technique in which the low molecular weight impurities are removed first, with a subsequent separation of the endotoxin from the polysaccharide, again, by size separation. Suitable size separation techniques include gel fitration, or more preferably, ultrafiltration. In the preferred embodiment of the invention, the polysaccharide arabinogalactan is first ultrafiltered using a 10,000 dalton membrane; the low molecular weight impurities (<10,000 da) are discarded. The retentate is ultrafiltered using a 100,000 dalton membrane; the high molecular weight retentate, which contains the endotoxin, is discarded, leaving a substantially purified endotoxin free arabinogalactan composition in the filtrate. Other polysaccharides such as dextran, mannan, and gum arabic are also well suited for this purification technique. The process and products produced thereby are well suited for use in parenteral pharmacuetical compositions.

8 Claims, 1 Drawing Sheet

ENDOTOXIN-FREE POLYSACCHARIDES

CROSS REFERENCE TO RELATED APPLICATIONS

This application is a continuation in part of U.S. application Ser. No. 08/260,551, filed Jun. 16, 1994, now U.S. Pat. No. 5,554,386, which is a continuation-in-part of application Ser. No. 936,873 filed Aug. 27, 1992, now U.S. Pat. No. 5,336,506 which is a continuation-in-part of application Ser. No. 900,686, filed Jun. 17, 1992, now U.S. Pat. No. 5,478,576, which is a continuation of Ser. No. 630,017, filed Dec. 19, 1990, now abandoned, which is a continuation in part of 679,526 filed Apr. 2, 1991, now U.S. Pat. No. 5,141,739, which is a continuation of Ser. No. 384,991, filed Jul. 2, 1989, now abandoned, which is a continuation in part of Ser. No. 228,640 filed Aug. 4, 1988, now abandoned, which is a continuation in part of Ser. No. 067,586, filed Jun. 26, 1987 now U.S. Pat. No. 4,827,945, which is a continuation in part of Ser. No. 882,044, filed Jul. 3, 1986, now U.S. Pat. No. 4,770,183, all of which are incorporated herein by reference.

FIELD OF THE INVENTION

The present invention is a process for preparing polysaccharides, such as arabinogalactan, in a chemically pure form with extremely low levels of bacterial endotoxins.

BACKGROUND OF THE INVENTION

Arabinogalactan obtained from the tree Larix occidentalis has a high affinity for a receptor found in hepatocytes termed the asialoglycoprotein receptor [Groman, E. V., P. M. Enriquez, et al. (1994). "Arabinogalactan for hepatic drug delivery."*Bioconjugate Chemistry* in press, incorporated herein by reference]. Materials attached to arabinogalactan are concentrated in hepatocytes after injection, including diagnostic agents like superparamagnetic iron oxide [Josephson, L., E. V. Groman, et al. (1990), "A functionalized superparamagnetic iron oxide colloid as a receptor directed MR contrast agent." *Mag Reson Imag* 8(5): 637–46; Reimer, P., R. Weissleder, et al. (1990). "Receptor imaging: application to MR imaging of liver cancer." *Radiology* 177(3): 729–34 both incorporated herein by reference), and therapeutic agents like the antiviral agent araAMP. Thus, arabinogalactan is useful as carrier of agents to hepatocytes in targeted drug delivery. Such applications require a highly purified, endotoxin free grade of arabinogalactan, which is the object of the current invention.

Chemistry of Endotoxin

Bacterial endotoxins are found in the outer membranes of gram negative Bacteria. A proposed structure of the endotoxin from salmonella is Hou, K. C. and R. Zaniewski (1990). "Depyrogenation by endotoxin removal with a positively charged depth filter." *J. Parenteral Science & Technology* 44(4): 204–209]. Endotoxin is termed lipopolysaccharide (LPA) consists of two general parts, a hydrophilic polysaccharide and a hydrophobic lipid component termed lipid A. Endotoxin can be an integral part of the bacterial membrane, however the molecule can dissociate from the membrane and exist in a wide variety of molecular weights. Apart from the bacteria, endotoxin can exist in forms as small as 10–20 kDa or in large aggregates or 0.1 um. The aggregation state of endotoxin depends on the presence of divalent cations (or chelators), and detergents.

The Need to Remove Endotoxin

To serve as a component of a parenteral pharmaceutical, a raw material must meet a number of criteria. It must be chemically homogeneous, since homogeneity assists in determining whether the material is identical from preparation to preparation. It must be well characterized chemically, and it must be free from impurities. Finally these chemical standards must be achieved at minimal cost.

Parenteral products, that is, products that are administered by intravenous, subcutaneous or intramuscular injection, must be free of bacterial endotoxins, which are lipopolysaccharides derived the outer membranes of gram-negative bacteria. The presence of endotoxins can cause fever, vasodilatation, and, in extreme cases, endotoxic shock. As early as 1970, the FDA required parenteral products be tested for endotoxin. Orally administered materials need not be endotoxin free, since endotoxins are present in high levels in the lumen of the gastrointestinal tract due to the presence of micro-organisms. However, the compositions suitable for parenteral administration must meet certain specifications for endotoxin levels. In the case of radiopharmaceuticals, the USP standard is 175 endotoxin units (eu) per dose (United States Pharmocopeia, 1995, p. 1489, incorporated herein by reference). Therefore, in the specification and accompanying claims, "substantially endotoxin free" means that the level of endotoxin is below the USP standard of 175 eu/dose.

Endotoxin contamination is a particular problem with many products of biological origin such as proteins, lipids, or polysaccharides, since these products can serve as growth media for micro-organisms. If sterility is not achieved during purification, microorganisms can multiply, release endotoxin and result in unacceptably high levels of endotoxin in the final product. For a review of the problem of endotoxin in biotechnology see [Sharma, K. S. (1986). "Endotoxin detection and elimination in biotechnology." *Biotechnolgoy and Applied Biochemistry* 8: 5–22], which, is incorporated herein by reference. The propensity for microbial growth during purification depends on the conditions utilized. Microbial growth is favored by a range of pH near neutrality, by the presence of nutrients, by a hospitable temperature, by the absence of microbial toxins, and other conditions. Standard methods of minimizing microbial growth and endotoxin contamination during purifications include (i) using sterile solutions and equipment to minimize the introduction of microorganisms, (ii) using filtration during purification, often with 0.45 micron or 0.22 micron filters, to remove micro-organisms, (iii) working at low temperature to minimize microbial growth, (iv) adding bacteriostatic agents to the purification. Obviously the practicality of these methods depends on the specifics of the purification. Except for sterile purification technique, i.e., one with all sterile components and perfumed in a sterile environment, some microbes are present, and hence endotoxin is often present in the final product. Since the cost of sterile purification is often prohibitive, it is desirable to have a method of separating the pure product from endotoxin as the final step. Some these methods for removing endotoxin are discussed below.

Methods of Removal of Endotoxin

The ease of separating endotoxin from the product depends in part on the similarities or differences between endotoxin and the product. For example, positively charged filters of various kinds have been widely used to remove negatively charged endotoxins [Hou, K. C. and R.

Zaniewski (1990). "Endotoxin removal by anion-exchange polymeric matrix." *Biotechnology and Applied Biochemistry* 12: 315–324], but such a separation cannot be utilized with a negatively charged product having characteristics similar to endotoxin. In addition endotoxin has a low density of negative charge, which can make removal inefficient.

Size based fractionation techniques like gel permeation chromatography or ultrafiltration can be utilized to separate endotoxin and product, provided that endotoxin is bigger or smaller than the product, see for example page 14 of Sharma, 1986. Size based techniques are hindered by the variety of molecular weights endotoxin can assume, see above. Consequently, membranes of different pore sizes are examined empirically, to find one with a pore size larger than the product yet smaller than the endotoxin in the aggregation state it has assumed.

Affinity chromatographic methods can be used, where endotoxin is removed by adsorption to the peptide antibiotic polymyxin B. While effective, such methods can be expensive.

The usefulness of arabinogalactan in hepatocyte targeted drug delivery, a parenteral pharmaceutical application, requires a method of producing a highly purified arabinogalactan with very low levels of endotoxin. Currently known methods of removing endotoxin are not practical for RME polysaccharides. Therefore, there is a need for an arabinogalactan preparation suitable for parenteral administration that is substantially free of endotoxin. There is a further need for a method of producing a parenterally administrable RME polysaccharide composition such as an arabinogalatan preparation, with minimal cost and at a scale suitable for industrial applications.

SUMMARY OF THE INVENTION

One of the objects of the invention is to produce a highly purified substantially endotoxin free preparation of an RME polysaccharide that is suitable for human or animal parenteral administration. In particular, the RME-polysaccharide can be mannan, gum arabic or preferably arabinogalactan. The substantially purified and endotoxin free arabinogalactan can be further described as the arabinogalactan composition that has a molecular weight such that the composition is first retained on 10,000 dalton membrane and will permeate a 100,000 dalton membrane. It is a further object of the invention to provide a method of producing a highly purified and substantially endotoxin free polysaccharide by first separating the polysaccharide from low molecular weight impurities by passing the polysaccharide composition through a fitter having a pore size smaller than the molecular weight of the polysaccharide and then separating polysaccharide containing fraction from the endotoxin fraction by passing the retentate through a second filter having a pore size sufficient to separate the polysaccharide from the endotoxin. The substantially endotoxin free material is collected as the filtrate. The process can include the steps of first filtering the polysaccharide though an 0.45 micron filter to remove large impurities before the filtration through the first filter. Preferably, the separation is done using an ultrafiltration membrane and more preferably, the polysaccharide is arabinogalactan, the first fitter has a 10,000 dalton pore size and the second filter has a 100,000 dalton pore size.

Another object of the invention is provide a method of removing endotoxin from polysaccharides which comprises the steps of filtering the polysaccharide through a 10,000 dalton membrane to remove low molecular weight impurities, then passing the retentate through a membrane having pores of a size sufficent to separate the endotoxin from the polysaccharide, and collecting the highly purified substantially endotoxin free material as the filtrate. This process can include the steps of first passing the unpurified polysaccharide through a 0.45 micron filter to remove large impurities before the 10,000 dalton filtration step is performed. The polysaccharide used in any of the methods of the invention can be mannan or gum arabic, and most preferably arabinogalactan. When arabinogalactan is the polysaccharide, the second membrane has a pore size greater than about 100,000 daltons.

DETAILED DESCRIPTION OF SPECIFIC EMBODIMENTS

Figure 1:
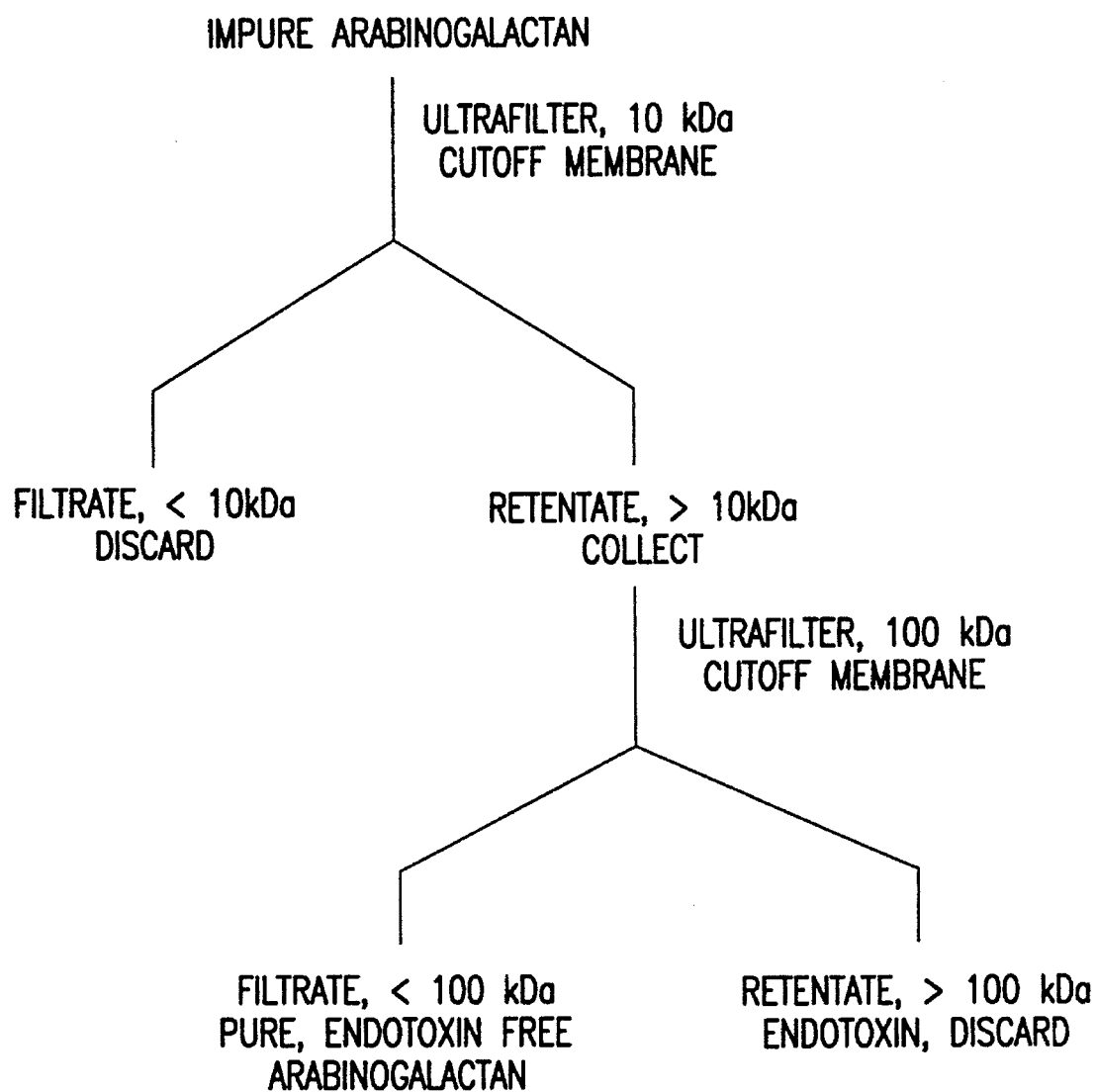
FIG. 1 is a flow chart showing the steps of producing a substantially endotoxin free arabinogalactan composition.

This invention provides a method of producing purified, substantially endotoxin free polysaccharides suitable for use in parenteral pharmaceutical applications. Among the types of polysaccharides amenable to this process are dextrans and dextran derivatives, and the RME polysaccharides, such as mannan, gum arabic and arabinogalactan.

A common method of obtaining arabinogalactan from the Larix occidentalis is by an aqueous extraction of wood chips, perhaps at elevated temperature, followed by treatment with magnesium oxide. The phenolic impurities including tannins adsorb to the MgO [Herrick, I., M, F. Adams, et al. (1967). Process of refining arabinogalactan containing compositions and product produced thereby. U.S. Pat. No. 3,326,473]. In an effort to obtain a more purified arabinogalactan, Adams found that after MgO treatment ultrafiltration could be employed to remove impurities which have higher or lower molecular weights than arabinogalactan Adams, M. F. and M. R. Knudson (1992). Ultrafiltered arabinogalactan product. U.S. Pat. No. 5,116, 969. Adams believed arabinogalactan to be present in variable molecular weight forms, with peaks at 50 and 90 kDa (column 1, line 41 ). A major impetus for utilizing ultrafiltration in this manner is the need to produce an arabinogalactan fully satisfactory for the density gradient separation of macromolecules (column 2, line 24 and column 4, line 25–46). Adams teaches that the order of membranes used is not crucial, column 7, line 30. In the method of Adams, microbial growth can occur during the extraction, MgO adsorption or ultrafiltration steps.

Ultrafiltration has the virtue of being easy to perform on large scale, and can remove high and low molecular contaminants from arabinogalactan. However, the ultrafiltration of arabinogalactan, while removing unwanted impurities, provides a particularly favorable environment for microbial growth. Micro-organisms can secrete enzymes which hydrolyze arabinogalactan to its component sugars (arabinose and galactose), or by utilizing other carbon sources present in the extract. Ultrafiltration of crude arabinogalactan, a mixture of saccharides and other molecules, is performed in water near neutral pH and at ambient temperatures. The purification of about a modest industrial quantity of 10 kg of arabinogalactan would require a volume of greater than 50 liters, assuming a maximum concentration of 200 mg/mL. At this scale, sterilization of the appropriate ultrafiltration apparatus and all solutions used, and/or reducing the temperature to a bacteriostatic 4° C., adds considerably to costs. Consistent with this, we have found that material prepared utilizing MgO treated arabinogalactan, followed by ultrafiltration can have high levels of endotoxin, see example 2 below.

We have discovered that the use of ultrafiltration membranes in a specific sequence during the purification of arabinogalactan can result in the elimination of endotoxin. This is highly surprising, since the fractionation of molecules according to size, such as by ultrafiltration, is not expected to yield this result. That is, eliminating small and large contaminants in any order would be expected to yield the same result. We have found that by first using a membrane with a pore size smaller than arabinogalactan, low molecular weight impurities are found in the filtrate and arabinogalactan in the retentate. When a membrane with a pore size larger than arabinogalactan is used, endotoxin is retained and arabinogalatan found in the filtrate (see FIG. 1 ). Use of the larger pore membrane first, followed by the smaller, failed to separate endotoxin from arabinogalacttan.

As was expected, the arabinogalactan obtained by either ultrafiltration method was free of high and low molecular weight impurities and had a similar size distribution. The endotoxin present is assayed by its activity in the sensitive lumulus amebocyte lysate (LAL) assay (Associates of Cape Cod, Falmouth Mass.), which can detect subnanogram quantities of endotoxin. Endotoxin comprises too small a percentage of the purified arabinogalactan to be recognized as an impurity with standard analytical techniques, We have discovered that the low molecular impurities present in the arabinogalactan preparation affect the aggregation state of the endotoxin. When those impurities are removed, as when the membrane smaller than arabinogalactan is used initially, the endotoxin undergoes a dramatic increase in size (aggregates). Thus when a membrane with a pore larger than arabinogalactan is used, the endotoxin is retained while the arabinogalactan passes through.

The method has the following advantages:

(i) It removes the endotoxin at the same time as the size dependent removal of chemical impurities performed by ultrafiltration is occurring. An additional treatment of arabinogalactan, such as with a positively charged filter or polymyxin column is not needed. Since the endotoxin is not removed by adsorption to a column or resin, there is no resin or support to dispose of or regenerate.

(ii) The endotoxin is removed as the last step of the chemical purification procedure. The purified arabinogalactan can be sterilized by filtration through a 0.22 micron membrane, and stored until dry.

(iii) Since it utilizes ultrafiltration, the method can be performed on a variety of scales.

Crude arabinogalactan can be obtained by extraction of wood chips by any of several techniques, [Adams, M. F. and M. R. Knudson (1992). Ultrafiltered arabinogalactan product. U.S. Pat. No. 5,116,969; Dahl, K. (1970). Recovery of high purity arabinogalactan from larch. U.S. Pat. No. 3,509, 126; DeWitt, J. E. (1990). Method of isolating arabinogalactan from larch. U.S. Pat. No. 4,950,751; Herrick, I. M. F. Adams, et al. (1967). Process of refining arabinogalactan containing compositions and product produced thereby. U.S. Pat. No. 3,326,473]. The arabinogalactan is filtered using a membrane large enough to retain the arabinogalactan but small enough to permit low molecular weight impurities to pass through. A 10 kDa membrane is widely available and satisfactory. Typically this is done by repeated additions of water and pressure filtration, or by dialysis against distilled water. The retentate is then passed through a membrane modestly larger than the arabinogalactan. A 100 kDa membrane is widely available and satisfactory.

Other devices that separate molecules by size can also be envisioned as being within the scope of this invention. For example, gel filtration columns can be used in sequence, where the unpurified polysaccharides are first eluted over a column that retains the low molecular weight material, followed by elution over a column that retains the high molecular weigh material, with the appropriate fractions being collected. Examples of such columns am Sephadex G-10 and G-100 columns.

EXAMPLES

Example 1:

A crude arabinogalactan termed as Stractan 2 was purchased from Champion Paper Company. This material is prepared by soaking wood chips from *Larix occidentalis* in water at about 70° C. using a counter current extraction procedure. The resulting crude liquor of arabinogalactan is then treated with MgO, and MgO removed by filtration.

The crude arabinogalactan is dissolved in water for injection and filtered through a series of membranes as necessary to remove particulate matter, e.g. a 5 and 1 micron membrane, followed by a 0.45 micron membrane to remove most micro-organisms. The arabinogalactan was then ultrafiltered through a 100 kDa membrane and the retentate, containing molecules greater than 100 kDa was discarded. The filtrate was collected and ultrafiltered against a 10 kDa membrane; the filtrate of this process containing molecules less than 10 kDa was discarded and the retentate collected. As a result, the material below 100 and above 10 kDa was obtained. The endotoxin was measured and found to be similar to that of the starting material, suggesting that much of endotoxin in crude arabinogalactan exists in an aggregation state such that it has molecular weight between 100 and 10 kDa. Since arabinogalactan has a molecular weight in this range, it would be expected that it would be impossible to separate endotoxin from arabinogalactan using ultrafiltration.

Example 2:

Example 1 was followed exactly as described except the order of ultrafiltration was changed. The 10 kDa membrane was used first, followed by the 100 kDa membrane. The endotoxin level was assayed by the LAL test, and was found to be less than 1.25 eu/mg arabinogalactan. If arabinogalactan were administered at 100 mg/arabinogalactan per dose, arabinogalactan purified by this method corresponds to 125 eu/dose, which is less than the 175 eu/dose limit specified by the USP.

We claim:

1. A method of making a highly purified, substantially endotoxin-free arabinogalactan composition which comprises the steps of:

(i) removing from an arabinogalactan-containing preparation by ultrafiltration, materials of a molecular weight that are less than the molecular weight of the arabinogalactan composition, and collecting the arabinogalactan-containing fraction thereof;

(ii) thereafter removing from the arabinogalactan-containing fraction by ultrafiltration, endotoxin and materials of a molecular weight that are greater than the molecular weight of the arabinogalactan; and (iii) collecting the resulting arabinogalactan-containing fraction, which has been rendered substantially endotoxin-free.

2. The method according to claim 1, wherein step (i) is preceded by the steps of:

(a) filtering the arabinogalactan through a membrane having a pore size no larger than 0.45 microns; and (b) collecting the filtrate containing the arabinogalactan for use in step (i).

3. The method of claim 2, in which ultrafiltration according to step (i) utilizes a membrane having a pore size which retains materials greater than 10,000 daltons and ultrafiltration according to step (ii) utilizes a membrane having a pore size which retains materials greater than about 100,000 daltons.

4. A method of removing endotoxin from an arabinogalactan solution which comprises;

(i) passing the arabinogalactan preparation through a first membrane having a pore size smaller than the size of the arabinogalactan, and collecting the retentate;

(ii) passing the retentate of step (i) through a second membrane, the second membrane having a pore size permitting passage of substantially all of the arabinogalactan while retaining the endotoxin; and (iii) collecting the filtrate produced in step (ii).

5. The method according to claim 4, in which step (i) is preceded by the steps of:

(a) filtering the arabinogalactan through a membrane having pores no larger than 0.45 microns; and (b) retaining the filtrate containing the arabinogalactan for use in step (i).

6. The method according to claim 5, in which the first membrane has a pore size which retains materials greater than 10,000 daltons and the second membrane has a pore size which retains materials greater than about 100,000 daltons.

7. A method of making a highly purified, substantially endotoxin-free arabinogalactan composition, which comprises the steps of:

(i) refining an unpurified arabinogalactan composition by ultra filtering the composition through a membrane; which removes materials below 10,000 daltons, and collecting the retentate of the ultra filtration process; and (ii) purifying the retentate of step (i) by ultrafiltration through a second membrane having a pore size greater than about 100,000 daltons; and (iii) collecting the filtrate produced in step (ii).

8. The method according to claim 7 in which refining the arabinogalactan compostion in step (i) is preceded by the steps of:

(i) filtering the arabinogalactan composition through a membrane having pores no larger than 0.45 microns; and (ii) collecting the filtrate containing the arabinogalactan composition.

* * * * *